US00PP08848P

United States Patent [19]

Guillen

[11] Patent Number: Plant 8,848

[45] Date of Patent: Jul. 26, 1994

[54] NEW GUINEA IMPATIENS NAMED BSR-220 BRIGHT CORAL

[75] Inventor: Mario Guillen, Cartago, Costa Rica

[73] Assignee: George J. Ball, Inc., West Chicago, Ill.

[21] Appl. No.: 133,966

[22] Filed: Oct. 8, 1993

[51] Int. Cl.[5] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-220 Bright Coral is provided. This new cultivar was the result of a controlled breeding program wherein the Diane cultivar (U.S. Plant Pat. No. 6,683) was pollinated by a plant designated N2298-1 (nonpatented in the United States). The new cultivar forms attractive large bright coral blossoms displaying an iridescent appearance combined with a good basal branching character and an upright growth habit and can be readily distinguished from the Dangal cultivar U.S. Plant Pat. No. 8,251).

1 Drawing Sheet

SUMMARY OF THE INVENTION

The present invention comprises a new and distinctive Impatiens plant, botanically known as New Guinea Impatiens, and hereafter referred to by the cultivar name BSR-220 Bright Coral.

The new cultivar is the product of a planned breeding program. More specifically, the breeding program which resulted in the production of the new cultivar was carried out in a controlled environment during 1990 at Linda Vista, Cartago, Costa Rica. The female parent (i.e., the seed parent) was the Diane cultivar (U.S. Plant Pat. No. 6,683) which exhibits salmon-red blossoms with dark green foliage. The male parent (i.e., the pollen parent) was a plant designated N2298-1 (nonpatented in the United States) which exhibits large deep salmon blossoms with dark green foliage. Such male parent was a proprietary breeding line of George J. Ball, Inc. The percentage of the new cultivar can be summarized as follows:

Diane × N2298-1.

The seeds resulting from the above pollination were sown and plantlets were obtained which were physically and biologically different from each other. Selective study resulted in the identification of a single plant of the new cultivar. This plant had large bright coral blossoms and initially was designated BSR-220.

It was found that the cultivar of the present invention:

(a) forms attractive very large bright coral blossoms displaying an iridescent appearance,
(b) exhibits a good branching character,
(c) exhibits an upright growth habit, and
(d) forms dark green laceolate foliage.

Asexual reproduction of the new cultivar by terminal or stem cuttings taken during 1991 at Arroyo Grande, Calif., U.S.A., has demonstrated that the characteristics of the new cultivar as herein described are firmly fixed and are retained through successive generations of such asexual propagation.

The BSR-220 Bright Coral cultivar has not been observed under all possible environmental conditions to date. Accordingly, it is possible that the phenotype may vary somewhat with variations in the environment, such as temperature, light intensity, and day length.

When the new cultivar of the present invention is compared to the Dangal cultivar (U.S. Plant Pat. No. 8,251), it is found that the new variety exhibits a growth habit which is not as low and compact and has larger leaves than the Dangal cultivar.

When plant material of the BSR-220 Bright Coral cultivar is subjected to standard random amplified polymorphic DNA marker analysis (RAPD) using polymerase chain reaction (PCR) and a known unique set of DNA primers, it is found to exhibit a different fingerprint map when compared to that of the Dangal cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is the R.H.S. Colour Chart of The Royal Horticultural Society, London, England. The color values were determined at West Chicago, Ill., U.S.A., during the first week of April, 1993. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Basal branching.

*Habit of growth.*—Upright mounded. A mature plant commonly measures approximately 17 to 18 cm. in height and approximately 23 to 24 cm. in width when grown in the greenhouse, and approximately 25 to 28 cm. in height and approximately 35 to 37 cm. in width when grown in the field. This can be compared to the dimensions of the Dangal cultivar which typically exhibits a height of approximately 15 to 16 cm. and a width of approximately 23 to 24 cm. when grown in the greenhouse, and a height of approximately 21 to 23 cm. and width of approximately 35 to 37 cm. when grown in the field.

*Foliage.*—The configuration is narrow and lanceolate. The leaves of the BSR-220 Bright Coral cultivar measure approximately 9.5 cm. × 3.5 cm. while those of the Dangal cultivar measure approximately 7.0 cm. × 3.0 cm. The foliage of the BSR-220 Bright Coral cultivar if Green Group 138B, with veins of Red Group 53A (abaxial) and Green Group 139A (adaxial). This can be compared to Yellow-Green Group 146B with veins of Red Group 53A (abaxial) and Green Group 137A (adaxial) for the Dangal cultivar. The stem color is Red Group 53A for both the BSR-220 Bright Coral cultivar and the Dangal cultivar.

Flower Description:

*Flowering habit.*—Freely flowering.

*Natural flowering season.*—Year-round in greenhouse environment.

*Flowers borne.*—Above foliage, arising from leaf axils.

*Flower color.*—Red Group 52B (abaxial) and Red Group 52A (adaxial). This can be compared to Red-Purple Group 58B (abaxial) and Red-Purple Group 57A (adaxial) for the Dangal cultivar.

*Quantity of Flowers.*—Approximately 8 to 10 per stem.

*Number of petals.*—Five.

*Flower Diameter.*—Approximately 6.5 to 7.0 cm. which can be compared to approximately 6.0 cm. for the Dangal cultivar.

*Flower length.*—Approximately 6.3 cm.

*Nectary length.*—Approximately 5.3 cm. which can be compared to approximately 6.5 cm. for the Dangal cultivar.

*Nectary color.*—Red Group 53B which can be compared to Red Group 53A for the Dangal cultivar.

*Reproductive organs.*—The anthers are fused together forming one organ that surrounds the pistil. Generally, the anthers shed pollen prior to the stigma becoming receptive. The pollen color is Yellow Group 10B which can be compared to a pollen color of Yellow Group 11C for the Dangal cultivar. The stigma color is Red Group 47B and can be compared to Red Group 42B exhibited by the Dangal cultivar. The ovary color is Yellow-Green Group 144A and can be compared to Yellow-Green Group 144C exhibited by the Dangal cultivar.

I claim:

1. A new and distinct cultivar of New Guinea Impatiens named BSR-220 Bright Coral, substantially as herein shown and described, which:

(a) forms attractive very large bright coral blossoms displaying an iridescent appearance,
(b) exhibits a good branching character,
(c) exhibits upright growth habit, and
(d) forms dark green lanceolate foliage.

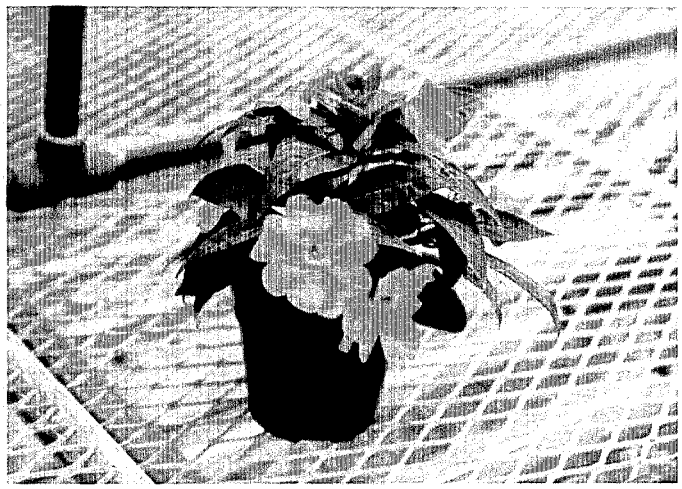

* * * * *